(12) United States Patent
Baccelli et al.

(10) Patent No.: US 7,503,918 B2
(45) Date of Patent: Mar. 17, 2009

(54) PLATE FIXING SYSTEM

(75) Inventors: Christian Baccelli, Saucats (FR); Paolo Mangione, Pessac (FR)

(73) Assignee: Abbott Spine, Austin, TX (US)

( * ) Notice: Subject to any disclaimer, the term of this patent is extended or adjusted under 35 U.S.C. 154(b) by 311 days.

(21) Appl. No.: 10/530,509

(22) PCT Filed: Oct. 2, 2003

(86) PCT No.: PCT/FR03/02890

§ 371 (c)(1),
(2), (4) Date: Apr. 6, 2005

(87) PCT Pub. No.: WO2004/032772

PCT Pub. Date: Apr. 22, 2004

(65) Prior Publication Data

US 2005/0273099 A1  Dec. 8, 2005

(30) Foreign Application Priority Data

Oct. 7, 2002  (FR) .................................. 02 12397
Feb. 28, 2003  (FR) .................................. 03 02503

(51) Int. Cl.
*A61B 17/56* (2006.01)
(52) U.S. Cl. ........................................ 606/61; 606/71
(58) Field of Classification Search ............. 606/61–73, 606/54, 60; 7/160, 169
See application file for complete search history.

(56) References Cited

U.S. PATENT DOCUMENTS

| | | | | |
|---|---|---|---|---|
| 5,443,464 A | * | 8/1995 | Russell et al. ................. | 606/54 |
| 5,443,467 A | * | 8/1995 | Biedermann et al. .......... | 606/65 |
| 5,573,536 A | * | 11/1996 | Grosse et al. .................. | 606/60 |
| 5,782,833 A | * | 7/1998 | Haider .......................... | 606/61 |
| 5,938,662 A | * | 8/1999 | Rinner .......................... | 606/60 |
| 6,368,320 B1 | * | 4/2002 | Le Couedic et al. ........... | 606/61 |
| 6,443,953 B1 | * | 9/2002 | Perra et al. .................... | 606/61 |
| 6,471,705 B1 | * | 10/2002 | Biedermann et al. .......... | 606/61 |
| 6,565,567 B1 | * | 5/2003 | Haider .......................... | 606/61 |
| 6,645,210 B2 | * | 11/2003 | Manderson ................... | 606/69 |
| 6,723,100 B2 | * | 4/2004 | Biedermann et al. .......... | 606/73 |
| 6,896,677 B1 | * | 5/2005 | Lin ............................. | 606/61 |

FOREIGN PATENT DOCUMENTS

| | | |
|---|---|---|
| FR | 2 812 535 | 2/2002 |
| FR | 2 827 757 | 1/2003 |
| WO | WO 97/37620 | 10/1997 |
| WO | WO 02/054966 | 7/2002 |

* cited by examiner

*Primary Examiner*—Eduardo C. Robert
*Assistant Examiner*—Tara George
(74) *Attorney, Agent, or Firm*—Sprinkle IP Law Group

(57) ABSTRACT

Disclosed is a system for immobilizing two vertebrae, which system includes two screws, and an elongated connecting member and two fastening systems. Each fastening system includes a clamping member and a fastening member consisting of a single ring-shaped piece having a lateral wall around an axial passage. The wall includes a first aperture for the clamping member and a second aperture comprising a first portion and a second portion. The first portion has a rim forming a bearing surface for the screw head. The second portion provides a free passage for the screw head. The axial passage can receive one end of the connecting member and the screw head, whereby (a) the screw head can be freely inserted into the axial passage of the fastening member and (b) the end of the connecting member and the screw head are immobilized by actuating the clamping member.

9 Claims, 8 Drawing Sheets

PLATE FIXING SYSTEM

BACKGROUND OF THE INVENTION

1. Field of the Invention

The present invention relates to a system for immobilizing two or more vertebrae relative to each other.

To be more precise, the present invention relates to a mechanical system that may be fitted by a surgeon to two or more vertebrae of the vertebral column in order to immobilize the at least two vertebrae relative to each other.

2. Description of the Prior Art

Systems of the above kind are known in the art. They comprise two pedicular screws that are screwed into the pedicles of the two vertebrae to be immobilized by an elongate member, usually referred to as a plate, whose ends are fixed to the heads of the two screws by mechanical fastening means so that the distance between the heads of the screws, and therefore the distance between the two vertebrae, remains fixed.

The screw heads are usually spherical in order to cooperate with the corresponding fastening means to form a ball-joint system allowing the plate to be fitted without applying stresses to the screws, and therefore to the vertebrae into which they are fixed, regardless of the relative direction of the two screws.

Clearly, one quality required of a system of the above kind is that the fastening of the plate and the screws should be sufficiently effective to be able to absorb the forces resulting from movements of the patient fitted with the immobilization system. Also, it is of course desirable for the system to be as easy for the surgeon to fit as possible, and for fitting it to require the shortest possible time on the operating table.

An object of the present invention is to provide a system of the type referred to above for immobilizing two or more vertebrae that constitutes a better response to the two conditions stated above.

SUMMARY OF THE INVENTION

To achieve the above object, the system of the invention for immobilizing two or more vertebrae comprises two or more screws, an elongate connecting member and two or more fastening systems and is characterized in that each screw comprises a screw body and a screw head having the shape of a portion of a sphere consisting of a first spherical surface portion between the screw body and a diametral plane orthogonal to the axis of the screw body and a second spherical surface portion; and each fastening system comprises at least:

a clamping member; and a fastening member formed in one piece having the shape of a ring having a lateral wall around an axial passage, said wall including a first aperture adapted to receive and to cooperate with said clamping member and a second aperture having a first portion and a second portion, said two portions communicating with each other and being angularly offset relative to the axis (Y, Y') of the fastening member, said first portion having a diametral axis (Z, Z') substantially coinciding with that of said first aperture and a rim forming a bearing surface for said first spherical surface portion of the screw head, said second portion of the second aperture allowing the screw head to pass through it, said axial passage being adapted to receive at least one end of said connecting member and said screw head, whereby the screw head may be freely introduced into the axial passage of the fastening member via said second portion of the second aperture by rotating said fastening member, the bearing surface of the first portion of the second aperture is made to face the first spherical surface portion of the screw head and, by activation of the clamping member, the end of the connecting member and the screw head are immobilized against rotation and against movement in translation relative to said fastening member.

Clearly, the system for fastening together the head of the pedicular screw and the elongate connecting member is really effective, because the clamping member presses the head of the pedicular screw with an appropriate force onto the bearing surface around the first portion of the second aperture, the axis of the clamping member and the axis of the aperture comprising the bearing surface substantially coinciding.

It is also clear that a fastening member that is made in one piece has a number of advantages: firstly, this avoids the surgeon needing to assemble a large number of parts under difficult operating conditions; secondly, the one-piece ring may have a smooth and regular exterior profile essentially free of asperities that could damage the surrounding human tissue.

It is further clear that the above immobilizing system is relatively easy to install since, after screwing the pedicular screws into the pedicles of the two vertebrae to be immobilized, the connecting member can easily be engaged over the head of each screw, thanks to the second part of the second aperture, and since it is also easy to lock the head of the screw into the fastening member, as it is sufficient to pivot the fastening member and to activate the clamping member.

In a preferred embodiment, said fastening system further comprises an intermediate member adapted to be inserted into the axial passage of the fastening member and having a first face adapted to be made to face the internal face of the wall of the fastening member, a recess opening onto said first face, forming a bearing surface for at least a portion of said second spherical surface portion of the screw head, and a second bearing face adapted to cooperate with the ends of the connecting member whereby, when said intermediate member is inserted into the axial passage of the connecting member, the clamping force produced by the clamping member is transmitted to said intermediate member via the end of the connecting member.

It is clear that in this preferred embodiment the clamping member clamps the head of the screw to the bearing surface via the intermediate member. The presence of this intermediate member enhances the quality of the contact between the intermediate member, to which the clamping force produced by the clamping member is applied, and the spherical head of the pedicular screw. In a preferred embodiment of this variant, the intermediate member may be premounted in the axial passage of the fastening member before it is used. The presence of this member therefore does not make the system for relative immobilization of vertebrae any more complicated to use.

BRIEF DESCRIPTION OF THE DRAWINGS

Other features and advantages of the invention become more apparent on reading the following description of embodiments of the invention given by way of non-limiting example. The description refers to the appended drawings, in which.

DETAILED DESCRIPTION OF THE PREFERRED EMBODIMENT(S)

Figure 1:
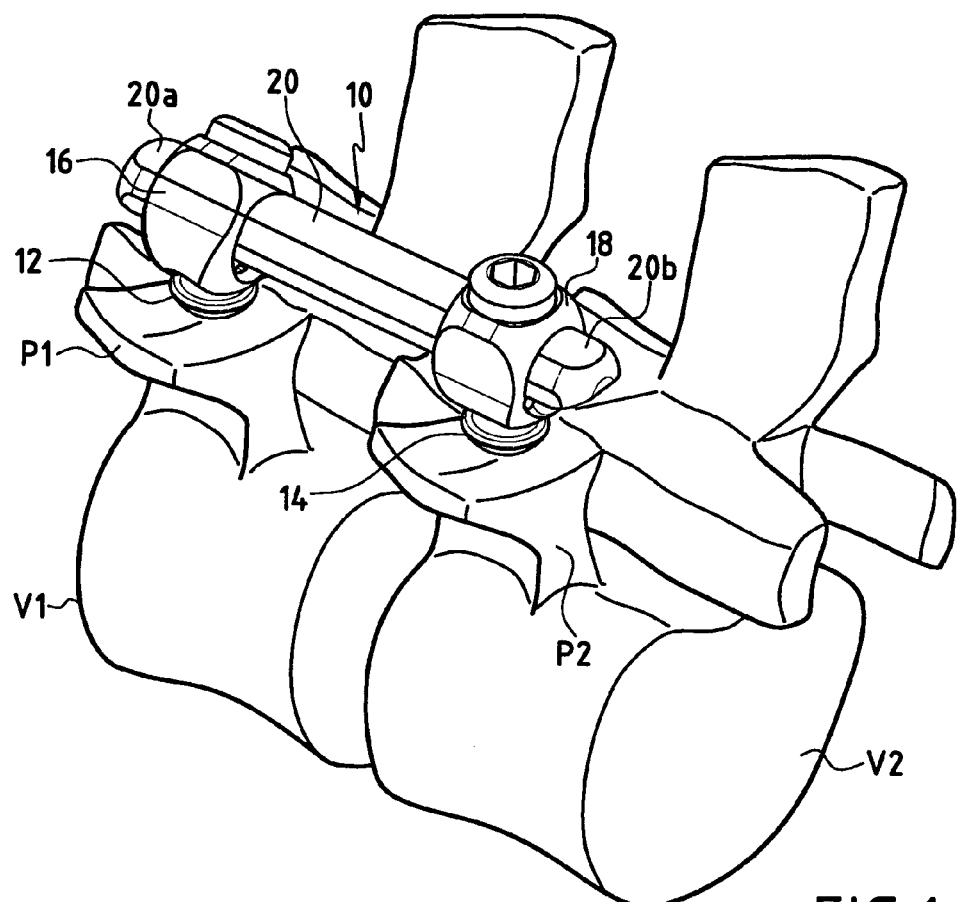
FIG. 1 is a perspective view showing the immobilization system fitted to two vertebrae.

The whole of the system for immobilizing two or more vertebrae is described first with reference to FIG. 1, after it has been fitted.

This figure shows a first vertebra V1 with its pedicle P1 and an adjacent second vertebra V2 with its pedicle P2. The immobilizing system 10 comprises a first pedicular screw 12 screwed into the pedicle P1, a second pedicular screw 14 screwed into the pedicle P2, a first fastening system 16 associated with the pedicular screw 12 and a second fastening system 18 associated with the pedicular screw 14. The immobilizing system 10 finally comprises an elongate connecting member 20 that is usually referred to as a plate. As this figure shows, each end 20a, 20b of the connecting member 20 is secured to the corresponding pedicular screw 12, 14 by a fastening system 16, 18. It is therefore clear that, by means of the connecting member 20, and by adjusting the distance between the fastening systems 16 and 18, after installing the screws 12 and 14, the surgeon can set a distance between the vertebrae V1 and V2.

Figure 2:
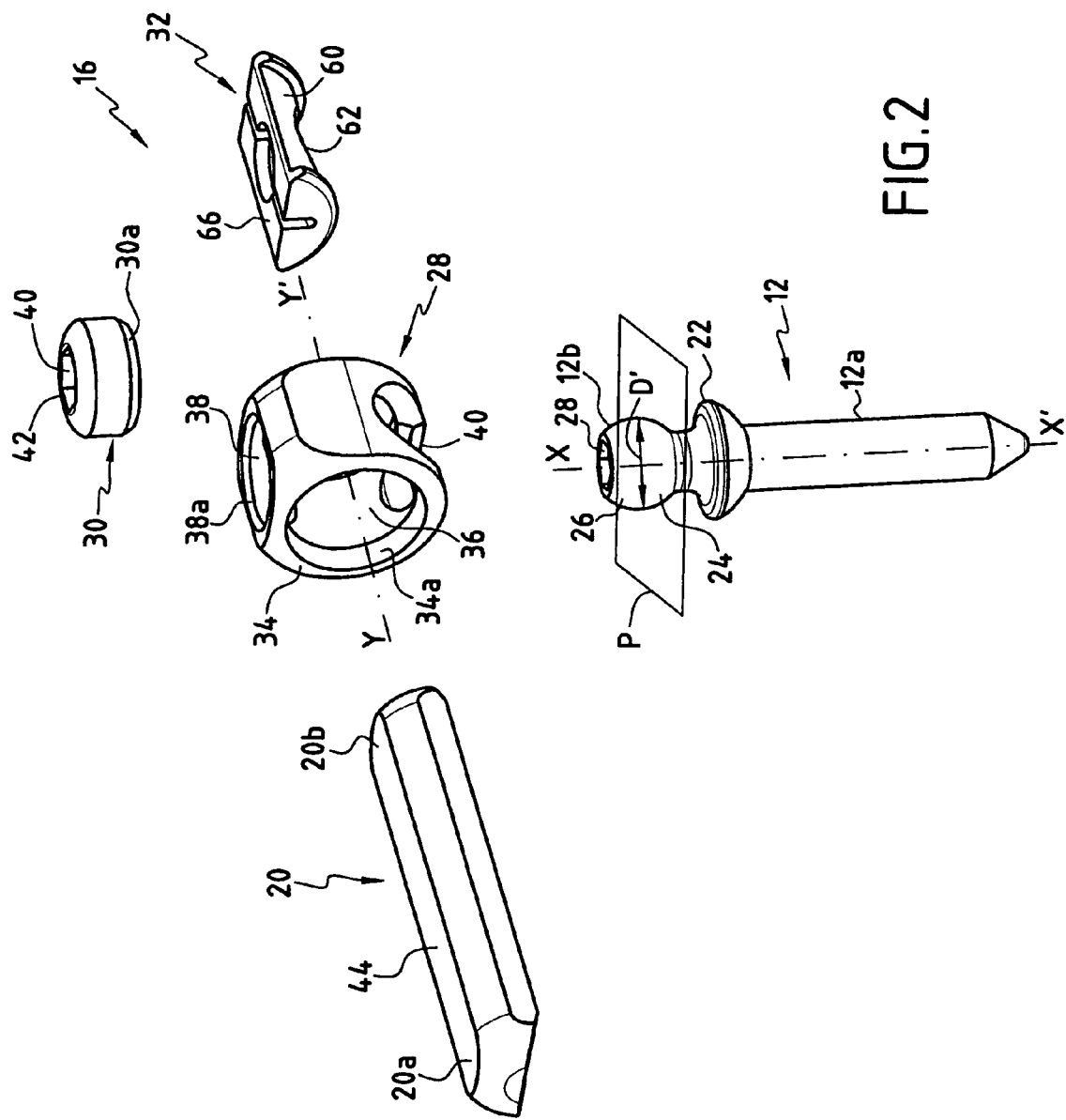
FIG. 2 is an exploded view of the components of the immobilization system.

The various component parts of the immobilizing system are described in more detail next with reference to FIG. 2. That figure shows the pedicular screw 12, which has a longitudinal axis X-X', a body 12a and a head 12b. The screw body 12a is preferably connected to the head 12b by a flange 22. The screw head 12b has a part-spherical surface divided by a diametral plane P perpendicular to the axis X, X' into a first spherical surface portion 24 between the plane P and the screw body 12a and a second spherical surface portion 26. The second spherical surface portion 26 is limited by a blind hole 38 of hexagonal or other shape adapted to receive a screwing tool. The fastening system 16 essentially consists of a fastening member 28, a clamping member 30 and, preferably but not necessarily, an intermediate member 32.

The fastening member 28 has the general shape of a ring consisting of a wall 34 whose internal face 34a is substantially a circular cylinder of revolution about an axis Y-Y'. This wall 34 of the member 28 has an axial passage 36 limited by the internal face 34a and two apertures 38 and 40 in the wall 34.

The first aperture 38 has a wall 38a that is tapped or constitutes part of a bayonet system. The aperture 38 is adapted to receive the clamping member 30, which has a portion 30a that is threaded or constitutes part of a bayonet system and a head 41 with a blind hole 42 for inserting a screwing or clamping tool, for example. FIG. 2 also shows the elongate connecting member 20, which has a substantially plane first face 44 adapted to cooperate with the active portion 30a of the clamping member 30. The portion 20, or at least each of its ends 20a and 20b, is adapted to be inserted into the axial passage 36 of the fastening member 28.

Figure 3:
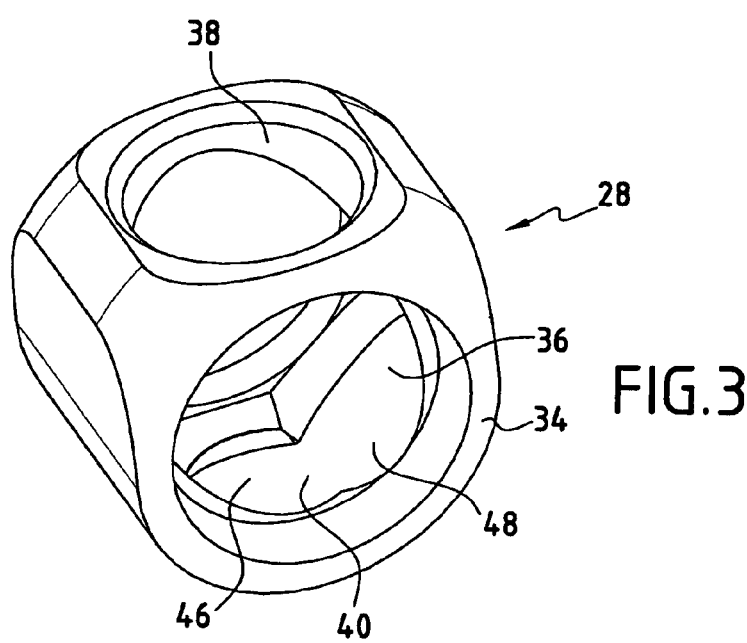
FIG. 3 is a perspective view of the fastening member.

The fastening member 28 is described in more detail next with reference to FIGS. 3 and 4A to 4C. FIG. 3 shows the wall 34 of this member with its cylindrical axial passage 36, its upper aperture 38 adapted to receive the clamping member 30 and its second aperture or lower aperture 40. FIG. 3 shows that the second aperture 40 in fact consists of two portions 46 and 48 that communicate with each other and are angularly offset relative to the axis Y, Y' of the fastening member.

Figure 4A:
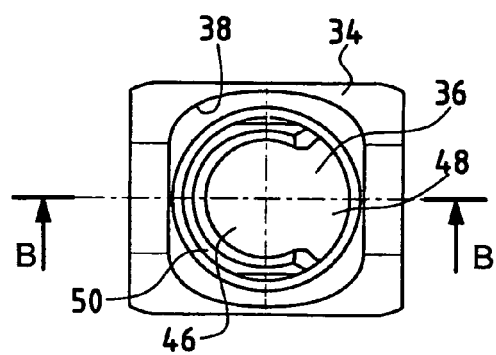
FIG. 4A is a top view of the fastening member.
Figure 4B:
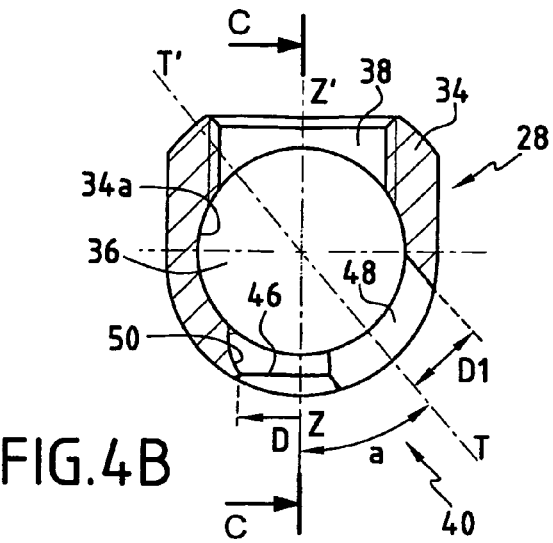
FIG. 4B is a view in section taken along the line B-B in FIG. 4A.
Figure 4C:
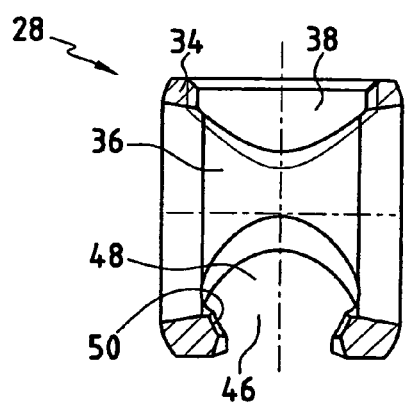
FIG. 4C is a view in section taken along the line C-C in FIG. 4B.

As shown better in FIGS. 4A and 4B, the first portion 46 of the second aperture 40 is in the shape of a portion of a circle (substantially a semicircle) whose axis Z-Z' coincides with the axis of the first aperture 38. This aperture portion 46 has a diameter D less than the diameter D' of the head 26 of the screw 12. The rim of the portion 46 of the aperture 40 constitutes a bearing surface 50 in the shape of a portion of a spherical surface, for example. The second aperture portion 48 is the shape of a portion of a circle of diameter D1 that has an axis T, T' offset at an angle a to the axis Z-Z'. The angle a may be 40 degrees. The diameter D1 of the second portion 48 of the aperture 40 is greater than the diameter D' of the head 26 of the screw 12. The contour of the second aperture 40 consists in the intersection of the circle portions corresponding to the aperture portions 46 and 48, of course. It is clear that the head 26 of the screw 12 may be freely inserted into the axial passage 26 of the fastening member 28 through the second part 48 of the aperture 40 when the axis X, X' of the screw is lined up with the axis T, T' of the aperture portion 48. If, however, the axis X, X' of the screw 12 is lined up with the axis Z-Z' of the fastening member 28, after inserting its head into the axial passage 36, the first spherical surface portion 24 of that head comes into contact with the spherical bearing surface 50, which "traps" the screw head in the axial passage 36.

Figure 5:
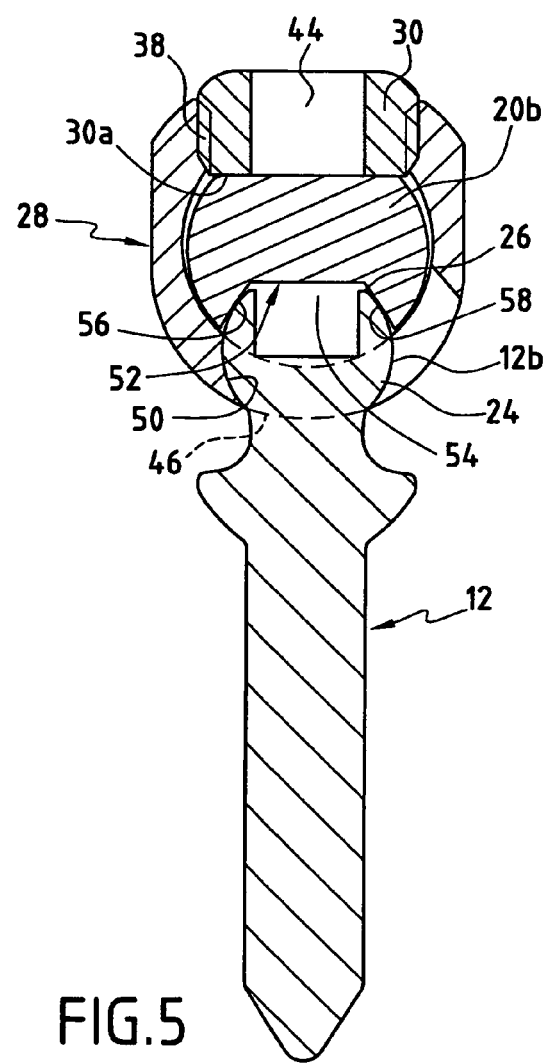
FIG. 5 is a view in vertical section showing the fastening together of a screw and the connecting member in a first embodiment of the invention.
Figure 6:
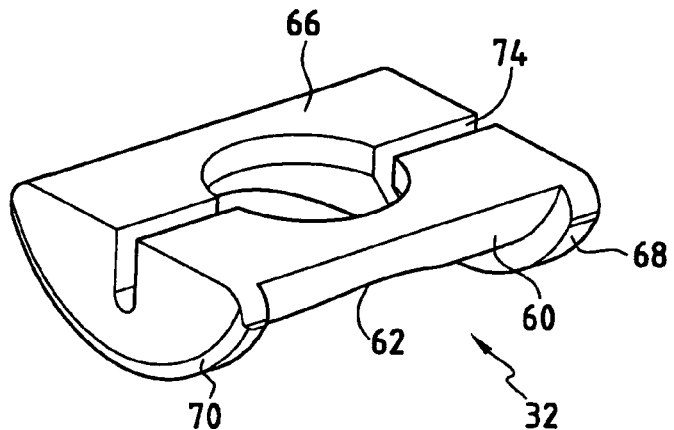
FIG. 6 is a perspective view of a first variant of the intermediate member.

FIG. 5 shows the assembled first embodiment of immobilizing device, i.e. the embodiment in which the fastening system does not include the intermediate member 32. This figure shows the screw 12 inserted in the first portion 46 of the second aperture 40 of the fastening member 28. The first spherical surface portion 24 of the screw head 12b therefore bears on the bearing surface 50 of this part of the aperture. In this embodiment, the second face 52 of the end 20b of the connecting member 20 includes a longitudinal recess 54 that defines two inclined longitudinal bearing surfaces 56 and 58. When the end 20b of the connecting member 20 is inserted into the axial passage 36 of the fastening member 28, the inclined bearing surfaces 56 and 58 of the member 20 face the second spherical surface portion 26 of the screw head 12b. When the clamping member 30 is screwed into its tapped aperture 38, the active face 30a is pressed against the plane face 44 of the member 20, which transmits the clamping force to the screw head 12b, which is immobilized against rotation by the cooperation of the bearing surfaces 50, 56 and 58. At the same time, this clamping immobilizes the member 20 against movement in translation relative to the fastening member 28.

In an improved embodiment of the immobilizing system, each fastening system 16, 18 further comprises an intermediate member 32 that can be inserted into the axial passage 36 of the fastening member 20.

A first preferred embodiment of the intermediate member 32 is described next with reference to FIGS. 6 and 7A to 7C. The intermediate member has a first face 60 in the shape of a portion of a cylindrical surface whose radius is substantially equal to that of the axial passage 36 of the fastening member 28. A recess 62 described in more detail later is formed in this first face 60. The second face 66 of the member 32 is substantially plane. The member 32 preferably has a rib 68, 70 at each end. The ribs are separated by an axial length L at least equal to the axial length of the member 28.

Figure 7A:
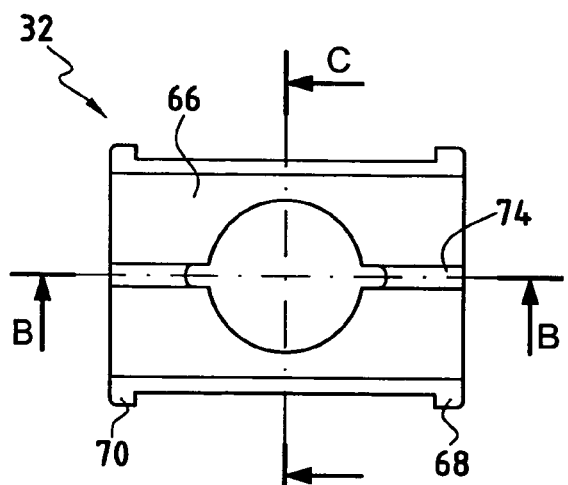
FIG. 7A is a top view of the FIG. 6 intermediate member.
Figure 7B:
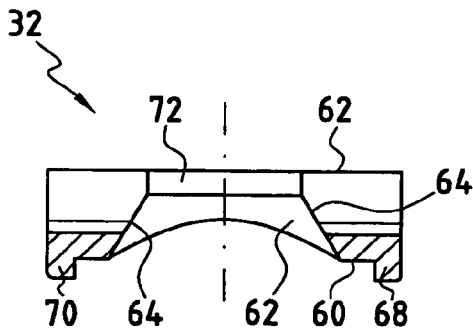
FIG. 7B is a view in section taken along the line B-B in FIG. 7A.
Figure 7C:
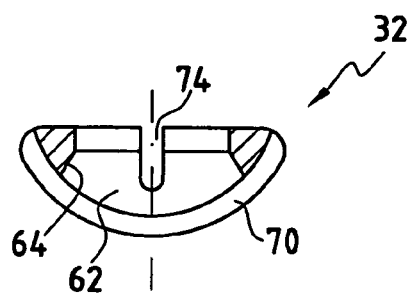
FIG. 7C is a view in section taken along the line C-C in FIG. 7A.

As shown better in FIG. 7B, the recess 62 formed in the member 32 has an active portion opening into the face 60 which constitutes a frustoconical, or possibly spherical, bearing surface 64. To facilitate machining, the active portion of the recess 62 is preferably extended by a circular part 72. It is also preferable if the member 32 includes a longitudinal groove 74 in its median longitudinal plane to enable it to deform elastically, as explained later.

The intermediate member 32 is inserted into the axial passage 36 in the fastening member 28 between the head 12b of the screw 12 and the ends 20a of the connecting member 20. The function of this part is to transmit the clamping force exerted by the clamping member 30 on the upper face 44 of the connecting member 20 to the second spherical portion 26 of the screw head 12b, by virtue of cooperation of the frustoconical bearing surface 64 of the recess 62 in the member 32 with the second spherical surface portion of the screw head 12b.

Figure 8C:
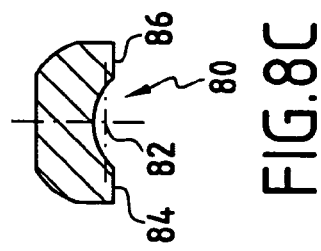
FIG. 8C is a view in section taken along the line C-C in FIG. 8A.
Figure 8A:
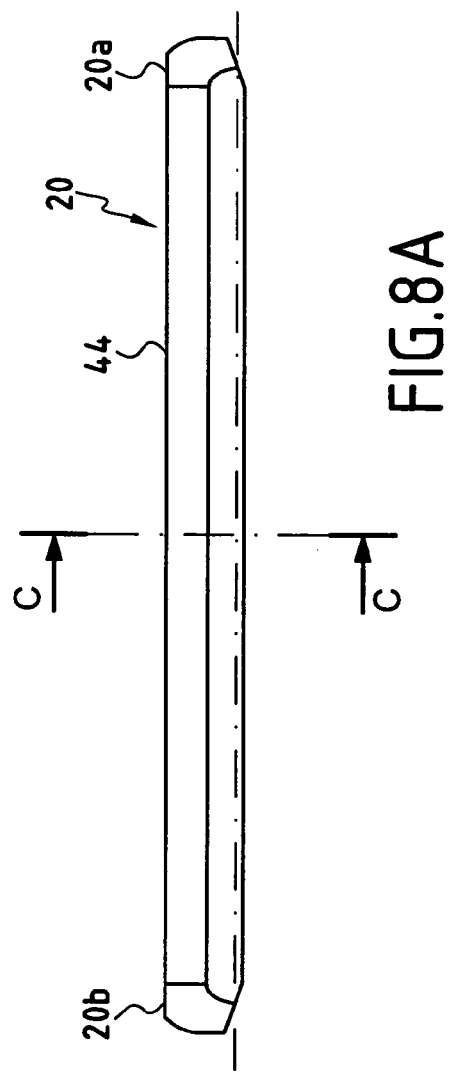
FIG. 8A is a view in longitudinal section of a first variant of the connecting member.
Figure 8B:
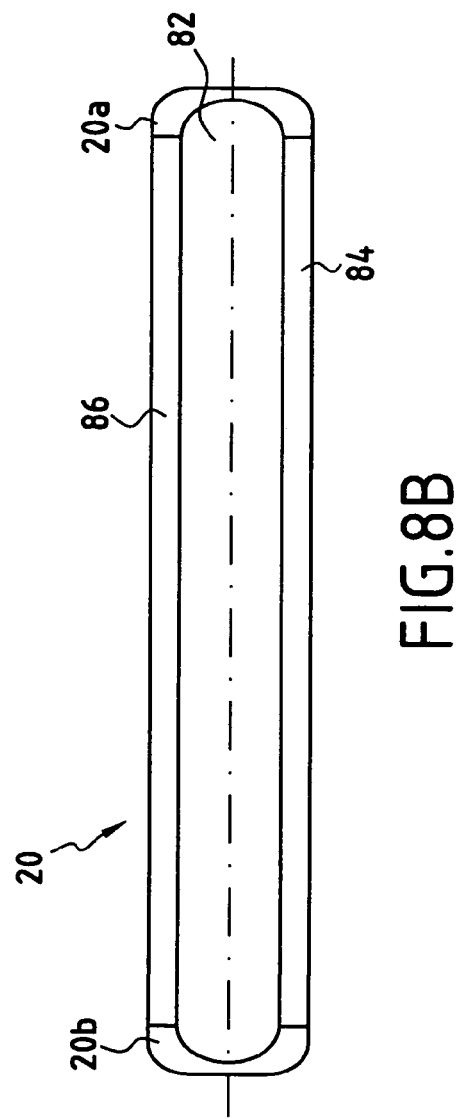
FIG. 8B is a bottom view of the FIG. 8A connecting member.

The particular shape of the connecting member 20 in the improved embodiment is described with reference to FIGS. 8A, 8B and 8C. The member 20 still has a plane upper face 44 and its second face 80 is also plane and includes an axial recess 82 such that this face 80 defines two longitudinal plane bearing surfaces 84 and 86. As explained later, these bearing surfaces 84 and 86 bear on the plane upper face 66 of the intermediate member 32.

Figure 9C:
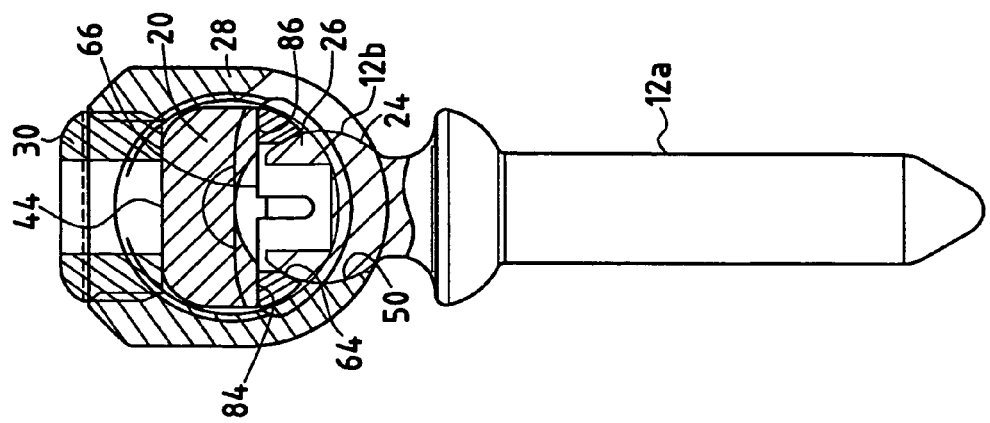
FIGS. 9A, 9B and 9C show the fastening together of a screw and the connecting member in an improved embodiment of the invention.

The use of the improved embodiment of the immobilization system is described next with reference to FIGS. 9A, 9B, 9C.

It should first be pointed out that the intermediate member 32 is preferably premounted inside the axial passage 36 of the fastening member and that the clamping member 30 is preferably premounted on the fastening member.

After screwing the screws 12 and 14 into the pedicles of the vertebrae to be immobilized, the surgeon fits the fastening members 28 over the heads 12b of the screws so that the axis T, T' of the second portion 48 of the second aperture 40 is aligned with that of the screw 12. The screw head 12b can pass freely through the aperture portion 48 and penetrate partially into the axial passage 36. To be more precise, the head 12b is accommodated inside the recess 62 of the intermediate member 32 which, at this stage, is free to pivot about the longitudinal axis of the fastening member. After carrying out this operation in respect of the screws 12 and 14, the surgeon fits the elongate connecting member 20 or, to be more precise, the ends 20A and 20B thereof, which have already been engaged in the fastening members 28.

Figure 9B:
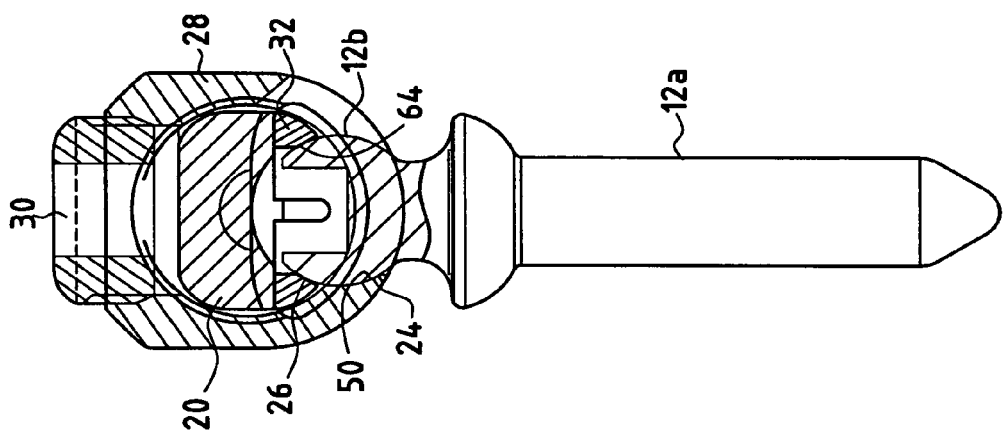
Figure 9A:
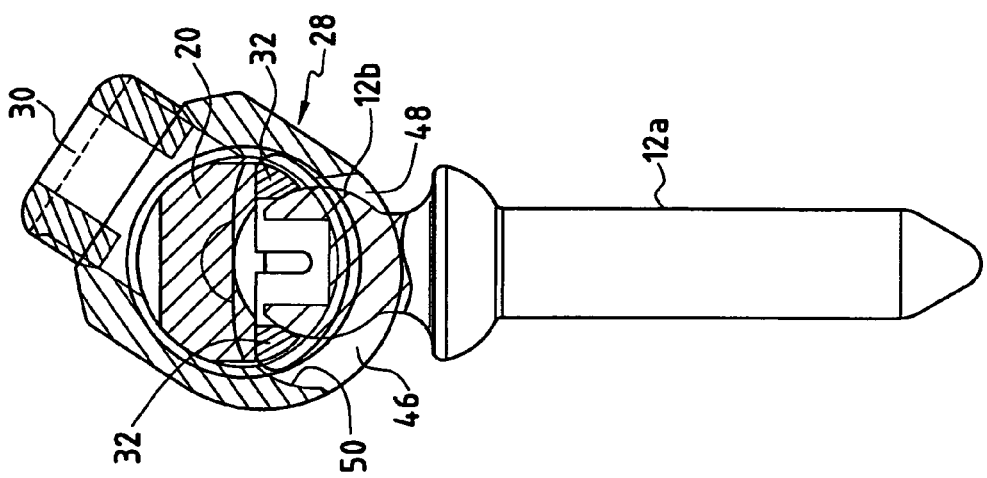

When these operations have been completed, the surgeon turns the fastening member 28 through the angle a about its longitudinal axis to align the axis Z, Z' of the first portion 46 of the aperture 40 with that of the screw 12 (see FIG. 9B). In this position, the first spherical surface portion 24 of the screw head 12b bears on the bearing surface 50 of the fastening member. It should be noted that, thanks to the ball-joint system formed by the screw head 12b and the spherical or conical bearing surfaces 50 of the portions 28, 64 of the intermediate member, the angular position of the elongate member 20 relative to the screws 12 and 14 may be adapted. When this operation has been completed, it suffices for the surgeon to activate the clamping members 30 of the two fastening members 28 to lock and immobilize the screw 12 and the connecting member 20 onto the fastening member 28.

Figure 12:
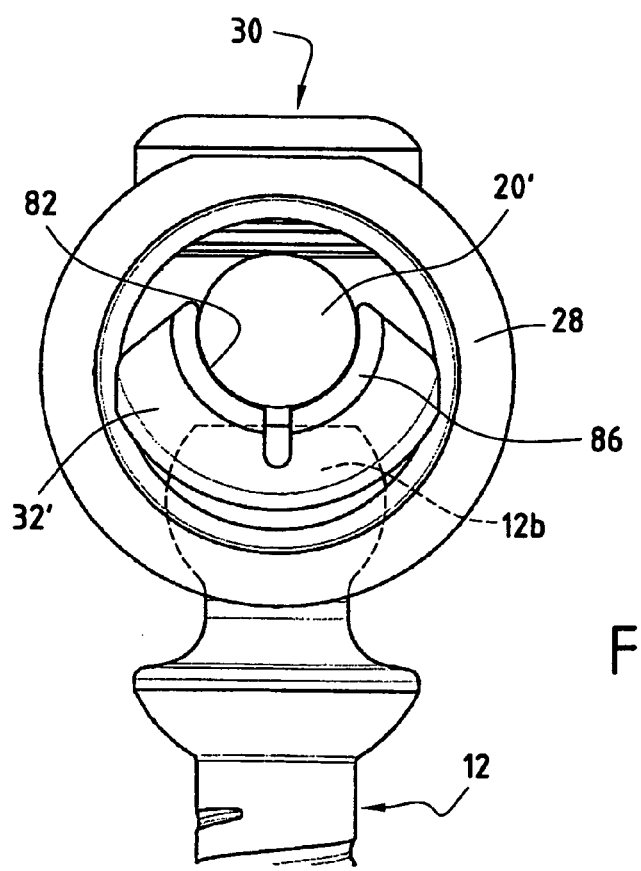
FIG. 12 is a view in elevation of the FIG. 10 variant.

A variant of the improved embodiment of the invention is described next with reference to FIGS. 10 to 12.

Figure 10:
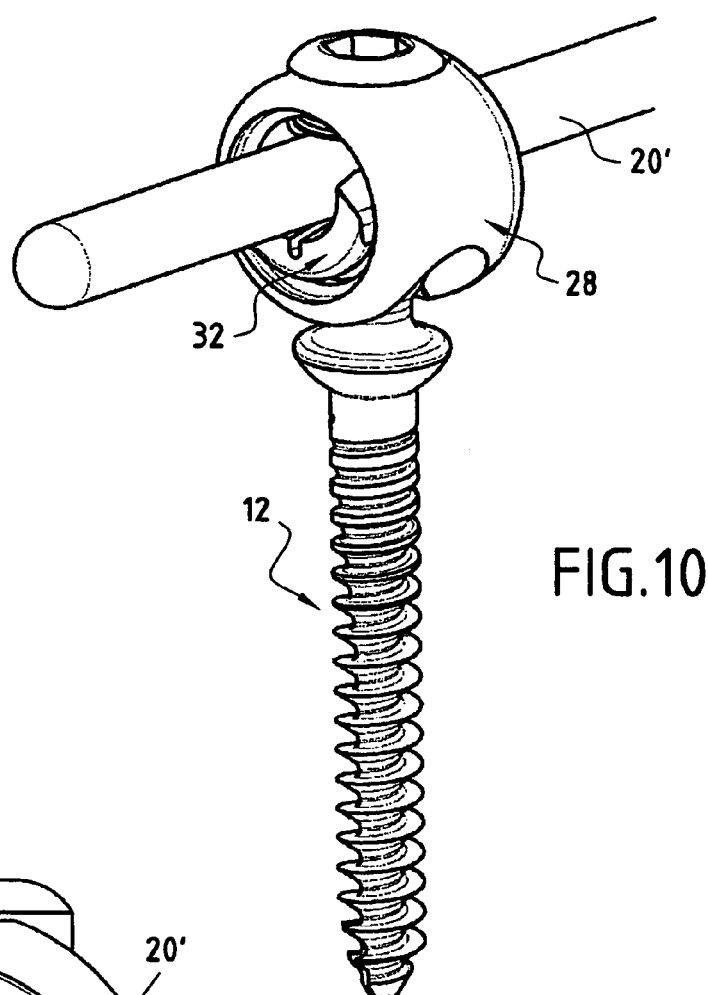
FIG. 10 is a perspective view of a second variant of the securing system.

This variant differs from the embodiment already described by virtue of the fact that the elongate connecting member 20' shown in FIG. 10 is a circular cross-section rod. Obviously, the intermediate member 32' shown in FIG. 10 must therefore be modified.

Nevertheless, the screws 12, the screwing member 30 and the fastening member 28 are not modified. They are therefore not described again.

Figure 11C:
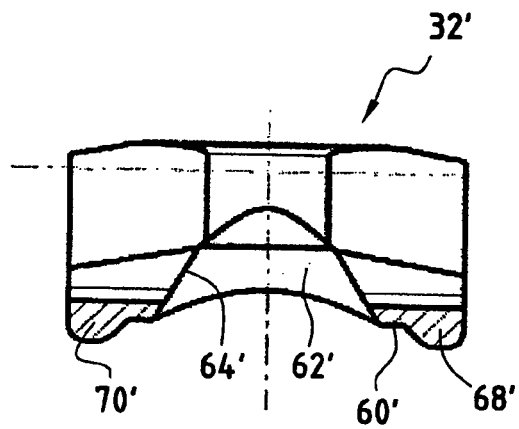
FIG. 11C is a view in section taken along the line C-C in FIG. 11B.
Figure 11D:
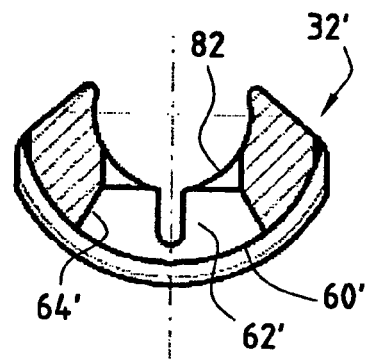
FIG. 11D is a view in section taken along the line D-D in FIG. 11B.
Figure 11B:
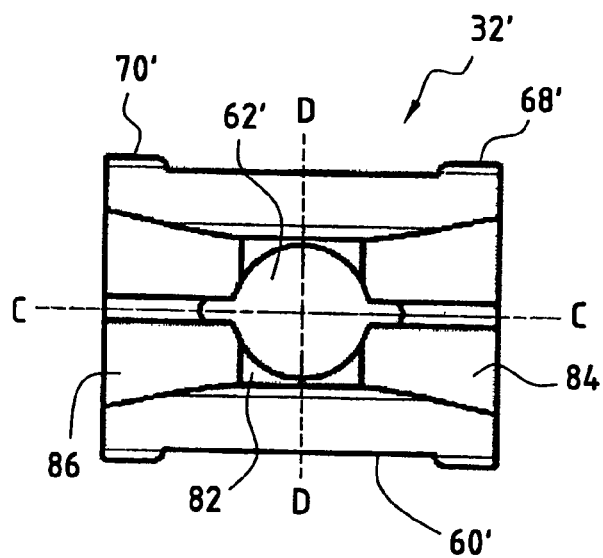
FIG. 11B is a top view of the FIG. 11A intermediate member.
Figure 11A:
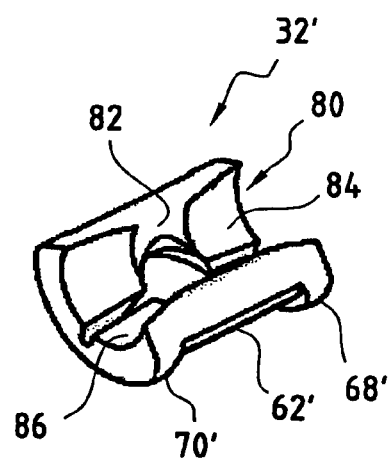
FIG. 11A is a perspective view of a variant of the intermediate member.

The variant of the intermediate member 32' is described with more particular reference to FIGS. 11A to 1D. The member 32' has a lower face 60' in the shape of a sector of a cylindrical surface adapted to be pressed against the internal wall 34 of the axial passage 36 in the fastening member 28. The lower face 60' terminates at its ends in ribs 68' and 70' that have the same function as the ribs 68 and 70.

A recess 62' in the lower face 60' of the member 32' has the same function as the recess 62 and includes a frustoconical or possibly spherical portion 64' adapted to bear on the spherical head 12b of the screw 12.

The upper face 80' of the member 32' includes a semicylindrical central bearing surface 82 conformed to receive the connecting rod 20'. The central bearing surface 82 is extended at both ends by semifrustoconical portions 84 and 86. The upper end of the recess 62' opens into the central bearing surface 82, which could equally well consist of two inclined plane surfaces symmetrical about the median plane of the member 32'.

This embodiment is used in substantially the same way as the embodiment shown in FIGS. 9A to 9D. The only difference is that the end of the connecting rod 20' is pressed onto the bearing surface 82 by the screwing member 30.

It follows from the foregoing description of the use of the securing system that the system facilitates installation, allows the necessary adaptation of the direction of the connecting member relative to the screws, and ensures secure and effective immobilization of the screws and the connecting member.

The invention claimed is:

1. A system for immobilizing two or more vertebrae, which system comprises two or more screws, an elongate connecting member and two or more fastening systems, wherein each screw comprises a screw body and a screw head having the shape of a portion of a sphere consisting of a first spherical surface portion between the screw body and a diametral plane orthogonal to an axis of the screw body and a second spherical surface portion; and each fastening system comprises:

a clamping member; and a fastening member formed in one piece having the shape of a ring having a lateral wall around an axial passage, said wall including a first aperture adapted to receive and to cooperate with said clamping member and a second aperture having a first portion and a second portion, said two portions communicating with each other, the first portion being angularly offset relative to the second portion about an axis (Y, Y') of the axial passage of the fastening member, said first portion having a diametral axis (Z, Z') substantially coinciding with that of said first aperture and a rim forming a bearing surface for said first spherical surface portion of the screw head, said second portion of the second aperture allowing the screw head to pass through it, said axial passage being adapted to receive at least one end of said connecting member and said screw head, whereby the screw head is introduced into the axial passage of the fastening member via said second portion of the second aperture by rotating said fastening member, with the bearing surface of the first portion of the second aperture made to face the first spherical surface portion of the screw head, the end of the connecting member and the screw head immobilized against rotation and against movement in translation relative to said fastening member.

2. The immobilization system according to claim 1, wherein said fastening system further comprises an intermediate member adapted to be inserted into the axial passage of the fastening member and having a first face adapted to be made to face the internal face of the wall of the fastening member, a recess opening onto said first face, forming a bearing surface for at least a portion of said second spherical surface portion of the screw head, and a second bearing face adapted to cooperate with the ends of the connecting member whereby, when said intermediate member is inserted into the axial passage of a connecting member, the clamping force produced by the clamping member is transmitted to said intermediate member via the end of the connecting member.

3. The immobilization system according to claim 1, wherein each end of said connecting member has a substantially plane first face and a second face including a longitudinal recess defining two inclined bearing surfaces adapted to cooperate with the second spherical surface portion of the screw head.

4. The immobilization system according to claim 2, wherein said intermediate member has at each end a rib projecting from its first face to cooperate with the end faces of said fastening member when the intermediate member is engaged in the axial passage of the fastening member.

5. The immobilization system according to claim 2, wherein each end of the connecting member has a substantially plane first face for cooperating with the clamping member and a second face defining two substantially plane bearing surfaces for cooperating with the second face of said intermediate member.

6. The immobilization system according to claim 4, wherein each end of the connecting member has a substantially plane first face for cooperating with the clamping member and a second face defining two substantially plane bearing surfaces for cooperating with the second face of said intermediate member.

7. The immobilization system according to claim 2, wherein said connecting member has a circular cross section and said second face of the intermediate member includes a bearing surface that has a cross section in the shape of a circular arc adapted to receive an end of said connecting member.

8. The immobilization system according to claim 4, wherein said connecting member has a circular cross section and said second face of the intermediate member includes a bearing surface that has a cross section in the shape of a circular arc adapted to receive an end of said connecting member.

9. The immobilization system according to claim 1, wherein the second portion has a diametral axis (T, T') offset at an angle "a" to the axis (Z, Z').

* * * * *